United States Patent
Kajihara et al.

(10) Patent No.: US 7,687,478 B2
(45) Date of Patent: Mar. 30, 2010

(54) DISIALOUNDECASACCHARIDE CHAIN ASPARAGINE/FATTY ACID AMIDE AND MEDICAL DRUG CONTAINING THE SAME

(75) Inventors: Yasuhiro Kajihara, Yokohama (JP); Hiroaki Maeda, Kyoto (JP); Kazuhiro Fukae, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 193 days.

(21) Appl. No.: 10/562,059

(22) PCT Filed: Jun. 29, 2004

(86) PCT No.: PCT/JP2004/009521

§ 371 (c)(1),
(2), (4) Date: Dec. 22, 2005

(87) PCT Pub. No.: WO2005/000906

PCT Pub. Date: Jan. 6, 2005

(65) Prior Publication Data

US 2007/0105813 A1  May 10, 2007

(30) Foreign Application Priority Data

Jun. 30, 2003 (JP) ............................. 2003-187931

(51) Int. Cl.
- *C08B 37/00* (2006.01)
- *C07H 5/04* (2006.01)
- *C07H 5/06* (2006.01)
- *A61K 31/715* (2006.01)

(52) U.S. Cl. ..................... 514/54; 536/55.1; 536/55.2
(58) Field of Classification Search ................ None
See application file for complete search history.

(56) References Cited

U.S. PATENT DOCUMENTS

2004/0181054 A1  9/2004  Kajihara et al. .......... 536/123.13

FOREIGN PATENT DOCUMENTS

EP  1 577 324 A1  9/2005

OTHER PUBLICATIONS

Merriam-Webster's Collegiate Dictionary, Tenth Edition, published by Merriam-Webster Incorporated, p. 924.*
Michel et al., "Model Glycoconjugates consisting of biantennary N-glycans coupled to fatty acids: Synthesis and X-ray diffraction study" Makromol. Chem. (1985) vol. 186, pp. 2365-2374.*
Remington: The Science and Practice of Pharmacy. Twentieth Edition, published 2000 by the Philadelphia College of Pharmacy and Science, pp. 735 and 860.*
FDA label for Tamiflu® (ostelamivir phosphate) revised Aug. 2001, published online at www.fda.gov.*
Drug Information: Zanamavir Inhalation, revised May 1, 2009, published online at http://www.nlm.nih.gov/medlineplus/druginfo/meds/a699021.html.*
Wilson et al., "Sequential Analysis of N- and O-Linked Glycosylation of 2D-PAGE Separated Glycoproteins" Journal of Proteome Research (2002) vol. 1 pp. 521-529.*
Ramos et al., "Characterization of the sugar-binding specificity of the toxic lectins isolated from *Abrus pulchellus* seeds" Clycoconjugate Journal (2001) vol. 18 pp. 391-400.*
Davoust et al., "Flexibility of bi- and triantennary glycans of the N-Acetyllactosaminic type" FEBS letters (1981) vol. 125 No. 2 pp. 271-276.*
Homans et al., "Solution conformation of the biantennary N-linked oligosaccharide of human serotransferrin using 'H NMR nuclear Overhauser effect measurements" FEBS Letters (1982) vol. 150 No. 2, pp. 503-506.*
Lowe, Mark et al., "The Structure of the Complex Type Oligosaccharide from Rabbit Hepatic Binding Protein," *The Journal of Biological Chemistry*, vol. 258, No. 3, pp. 1885-1887, 1983.
Endo, Masahiko et al., "The Structures and Microheterogeneity of the Carbohydrate Chains of Human Plasma Ceruloplasmin," *The Journal of Biological Chemistry*, vol. 257, No. 15, pp. 8755-8760, 1982.

* cited by examiner

*Primary Examiner*—Shaojia Anna Jiang
*Assistant Examiner*—Eric S Olson
(74) *Attorney, Agent, or Firm*—Myers Bigel Sibley & Sajovec, P.A.

(57) ABSTRACT

An asparagine-linked disialoundecaoligosaccharide-fatty acid amide, a drug containing the same, and a drug containing an asparagine-linked disialoundecaoligosaccharide.

22 Claims, 5 Drawing Sheets

Fig. 2 asparagine-linked disialoundecaoligosaccharide-decanoic acid amide 3 asparagine-linked disialoundecaoligosaccharide-myristic acid amide 4 asparagine-linked disialoundecaoligosaccharide-stearic acid amide 5 asparagine-linked disialoundecaoligosaccharide-behenic acid amide 6

Fig. 3

Fig.4 sialidase inhibition activity of each inhibitor
against Dansyl- LacNAc-NeuAc
(IC$_{50}$ based on the amount of sialic acid in each inhibitor)

abbreviation
    NeuAc-Lactose : sialyl lactose
    Disialo-Asn : asparagine-linked disialoundecaoligosaccharide 1
    Disialo-Asn-10 : asparagine-linked disialoundecaoligosaccharide-decanoic acid amide 3
    Disialo-Asn-14 : sparagine-linked disialoundecaoligosaccharide-myristic acid amide 4
    Disialo-Asn-18 : asparagine-linked disialoundecaoligosaccharide-stearic acid amide 5
    Disialo-Asn-22 : asparagine-linked disialoundecaoligosaccharide-behenic acid amide 6

IC$_{50}$ of each inhibitor
    NeuAc-Lactose : 295.5 μM
    Disialo-Asn : 428.3 μM
    Disialo-Asn-10 : 318.5 μM
    Disialo-Asn-14 : 186.4 μM
    Disialo-Asn-18 : 117.9 μM
    Disialo-Asn-22 : 42.9 μM

Fig.5 sialidase inhibition activity of each inhibitor
against Dansyl- LacNAc-NeuAc
(IC$_{50}$ based on the mole concentration of each inhibitor)

IC$_{50}$ of each inhibitor

NeuAc-Lactose : 295.5 μM    Disialo-Asn-14 : 93.2 μM
Disialo-Asn : 214.2 μM    Disialo-Asn-18 : 58.9 μM
Disialo-Asn-10 : 79.6 μM    Disialo-Asn-22 : 21.5 μM

DISIALOUNDECASACCHARIDE CHAIN ASPARAGINE/FATTY ACID AMIDE AND MEDICAL DRUG CONTAINING THE SAME

This application is a 371 of international application PCT/JP2004/009521, which claims priority based on Japanese patent application No. 2003-187931 filed Jun. 30, 2003, which is incorporated herein by reference.

TECHNICAL FIELD

The present invention relates to asparagine-linked disialoundecaoligosaccharide-fatty acid amide, and a composition or a drug containing the same.

BACKGROUND ART

Influenza is an infectious disease which is-prevalent in the world almost every year. Many people are infected with influenza every year despite the existence of vaccine and suffer from fever, headache, musculus arthralgia and the like. Further they are inflicted with complications, i.e. influenza brain inflammation and encephalopathy and may die of the complication in the worst case. The influenza virus is so feared despite the existence of vaccine because influenza virus tends to cause gene mutation, leading to change of antigen form so that the antibody increased in the body by vaccine fails to recognize it, and the effect of vaccine is lowered. As described above, even if it is predictable what type of influenza will prevail every year, a problem is raised in that a proper vaccine can not be rapidly supplied since a new type of virus will be generated all at once. In this situation, it is necessary to develop a highly effective drug which can show high effects on various kinds of influenza viruses. In recent years, the infection mechanism of influenza viruses have been clarified in terms of molecule levels and gene levels due to marked progress of scientific technology. It is now under way to prepare various kinds of influenza virus infection inhibitors.

The infection of influenza viruses and the mechanism of growth are as follows. First, a virus is made to invade the living body. On approaching the host cell, a trimer of protein called hemagglutinin on the outer layer of the virus, becomes specifically bonded to a sialyl oligosaccharide, i.e. a receptor on the host cell. The sialyl oligosaccharide contains sialic acid at the end. The sialic acid is chiefly involved in bonding to hemagglutinin. Then a membrane fusion occurs between the virus and the host cell so that the virus makes RNA infected with the host cell. Then, the virus gene is replicated therein for the advent of virus offspring. Then, a virus is germinated outside the host cell to complete the propagation. In germination of a virus, hemagglutinin becomes bonded to sialyl oligosaccharide again. The sialic acid is separated from the sialyl oligosaccharide by sialidase, namely an enzyme, on the outer layer of the same virus, whereby germination can be achieved.

Recently new remedies have been developed for inhibiting the activity of sialidase reaction occurring at the last stage of virus infection. These two drugs are available under the names Zanamivir (trade name, Relenza, Glaxo Wellcome) and Oceltamivir phosphate (trade name, Tamiflu, Japanese Roche Corp.). However, these two sialidase inhibitors are able to inhibit the infection at the last stage of infection and are less effective in inhibition because it acts after the growth of a virus has reached the peak. It is desirable to administer the drug within 48 hours after development of infection. Therefore, a compound useful as an effective drug is demanded which inhibits the infection at the first stage at. which the virus is bonded to the host cell.

It is already known that in the development of hemagglutinin inhibitors, when a polyvalent sialyl oligosaccharide derivative having a number of sialyl oligosaccharides in a molecule shows a higher inhibiting activity against an influenza virus than a monovalent sialyl oligosaccharide derivative. This is because an affinity between a ligand and a receptor is more increased when polyvalent molecules having a plurality of sialyl oligosaccharide derivatives are bonded thereto than when plural monovalent sialyl oligosaccharide derivatives are bonded to numerous hemagglutinins existing on the surface of the virus.

Up to date, a multiplicity of polyvalent sialyl oligosaccharide derivatives have been developed with the expectation of such effect. Kanie et al prepared a styrene polymer (1) having sialyl lactose bonded thereto and researched the relation of the polymer with influenza. It was found that the polymer exhibits inhibition activity 1,000 times as high as fetuin which is a sialyl oligosaccharide protein.

(1)

Whitesides et al synthesized a polyacrylamide polymer (2) having a sialic acid derivative bonded and showed that the higher the molecular weight of the polymer is, the higher the inhibition activity is.

R=H or NeuAc derivative

However, the polymer, i.e. high molecular weight compound, is a mixture of polymers having different molecular weights and thus has a structure which is not clear. If the compound contains a polymer having a molecular weight of 60 KDa or higher, the polymer remains in the body since it has too high a molecular weight to be removed from the body. Specifically it can not be passed through Bowman's capsules in Malpighian corpuscles of the kidney, so that the balance of metabolism in the liver is thrown. Thus, the defect is likely to do harm to the human body. For this possibility, FDA (The Food Drug Administration) does not approve the compounds like such polymer type for the safety problem even if the compound is an effective influenza infection inhibitor. An object of the invention is to provide a novel asparagine-linked disialoundecaoligosaccharide-fatty acid amide, and a composition or a drug containing the same.

Another object of the invention is to provide a drug for preventing and/or curing virus diseases such as influenza virus. infectious diseases, the drug having a high activity of inhibiting the virus infection and/or the growth.

DISCLOSURE OF THE INVENTION

The invention provides an asparagine-linked disialoundecaoligosaccharide-fatty acid amide.

The invention provides a composition or a drug containing the asparagine-linked disialoundecaoligosaccharide-fatty acid amide.

The invention also provides a drug containing an asparagine-linked disialoundecaoligosaccharide.

The asparagine-linked disialoundecaoligosaccharide-fatty acid amide of the invention is a compound which can be prepared by reacting an asparagine-linked disialoundecaoligosaccharide with a fatty acid.

The asparagine-linked disialoundecaoligosaccharide is an asparagine-linked oligosaccharide (3) shown below.

This asparagine-linked disialoundecaoligosaccharide can be prepared, e.g., according to Reference Example 1 of Japanese Patent Application No. 2002-196821.

Examples of the fatty acid constituting the fatty acid amide in the invention are aliphatic saturated or aliphatic unsaturated fatty acids having 6 to 32 carbon atoms and combinations of at least two kinds thereof. Examples of the aliphatic saturated fatty acids include straight chain or branched chain hexanoic acid (caproic acid, 2-ethyl butanoic acid and so on), heptanoic acid (enanthic acid and so on), octanoic acid (caprylic acid, 2-ethylhexanoic acid and so on), nonanoic acid (peralgonic acid and so on), decanoic acid (capric acid and so on), undecanoic acid, (undecylic acid and so on), dodecanoic acid (lauric acid, 2-ethyldecanoic acid and so on), tridecanoic acid (tridecylic acid and so on), tetradecanoic acid (myristic acid and so on), hexadecanoic acid (palmitic acid and so on), octadecanoic acid (stearic acid and so on), eicosanic acid (arachic acid and so on), docosanoic acid (behenic acid and so on), and tetracosanoic acid (lignoceric acid and so on).

Examples of the aliphatic unsaturated fatty acids include straight chain or branched chain octenoic acid, decenoic acid, undecenoic acid, (undecylenic acid and so on), dodecenoic acid, octadecenoic acid (oleic acid, eraidic acid and so on), linoleic acid, linolenic acid and so on. Among these fatty acids, preferred are fatty acids having 8 to 24 carbon atoms, and more preferred are those having 10 to 22 carbon atoms, especially preferred are decanoic acid, dodecanoic acid, tetradecanoic acid, hexadecanoic acid, octadecanoic acid, eicosanic acid, docosanoic acid and octadecenoic acid. Among them, most preferred are straight chain fatty acids such as capric acid, lauric acid, myristic acid, palmitic acid, stearic acid, arachic acid, behenic acid and oleic acid.

The asparagine-linked disialoundecaoligosaccharide is reacted with the fatty acid preferably in the presence of a reaction activator. Useful reaction activators are N-hydroxysuccinimide, N-hydroxybenzotriazole (HOBT) and so on.

The asparagine-linked disialoundecaoligosaccharide is reacted with the fatty acid in a ratio of 1 mole of asparagine-linked disialoundecaoligosaccharide and preferabyl about 0.1 to about 10 moles of the fatty acid. The reaction activator is preferably used in an amount of about 0.1 mole to about 10 moles per mole of asparagine-linked disialoundecaoligosaccharide. The reaction is usually conducted at 0 to 80° C., preferably 10 to 60° C., and is usually completed in about 10 minutes to about 5 hours.

The asparagine-linked disialoundecaoligosaccharide-fatty acid amide thus obtained can be purified, e.g., by filtration, high performance liquid chromatography (HPLC) or the like. These compounds can be identified by NMR, HPLC (ODS column), etc. in which the detection time in UV is determined.

Figure 1:
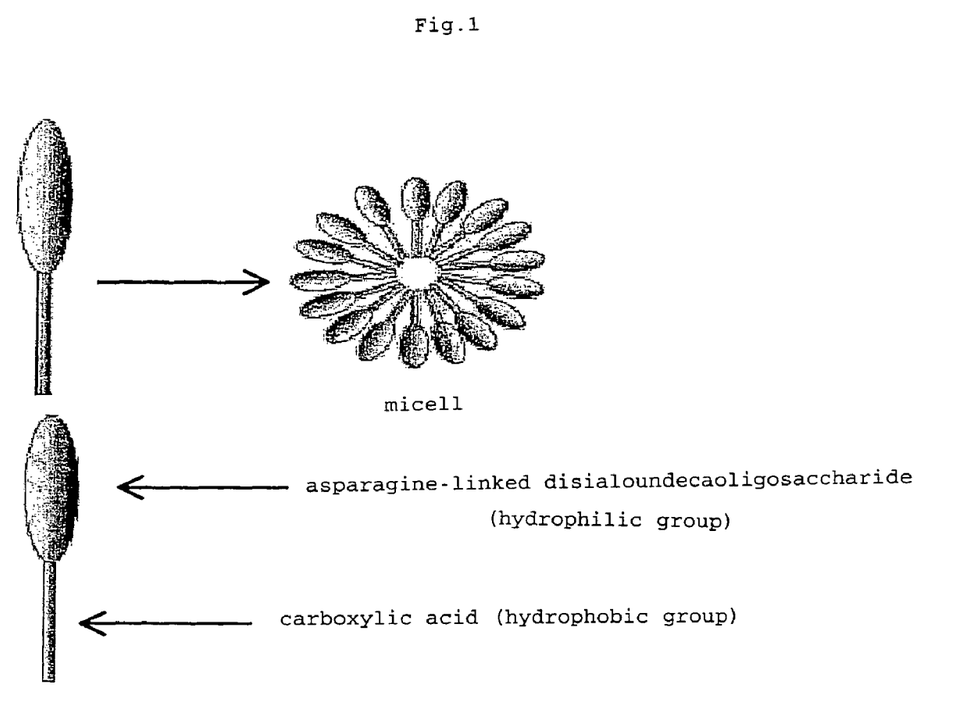
FIG. 1 shows a micell of asparagine-linked disialoundecaoligosaccharide-fatty acid amide.

The asparagine-linked disialoundecaoligosaccharide-fatty acid amide of the invention has both a hydrophilic group of asparagine-linked disialoundecaoligosaccharide and a hydrophobic group of fatty acid having a long carbon chain, so that a micell can be easily created in an aqueous solution as shown in FIG. 1, and a polyvalent asparagine-linked oligosaccharide derivative can be obtained which is of a low molecular weight type and which is clear in terms of molecular weight and structure.

In this way, a compound limited to a low molecular weight range can be produced more relatively easily than a polymer without difference in molecular weight by utilizing the production of a micell of monovalent molecules. Thus, for example, the obtained compound can exhibit a high inhibiting activity against an influenza virus by the creation of a micell and forming polyvalent molecules.

The drug of the invention contains as an effective component the forgoing asparagine-linked disialoundecaoligosaccharide-fatty acid amide. Further, the drug of the invention contains as an effective component the asparagine-linked disialoundecaoligosaccharide.

The drug of the invention is provided in the form of a pharmaceutical composition comprising the foregoing effective component and pharmaceutical additives (carriers, excipients and so on). Useful carriers include, for example, lactose, glycerin and so on. Useful excipients are, for example, lactose, glucose, sucrose, mannitol and so on. The amount of the effective component to be used in the drug is about 0.01 to about 95 wt %, preferably about 1 to about 80 wt %.

The administration route of the drug of the invention is not limited. An oral route or a parenteral route is employed. Parenteral administrations are, for example, intramascular, intravenous, subcutaneous and intraperitoneal administrations, applications of mucous membranes to nasal cavity, inhalation administration and so on. The form of the drug according to the invention is not limited. The form of the drug for oral administration is, for example, tablets, capsules, fine grains, powders, granules, solutions, syrups, etc. Examples of the formulations for parenteral administration are injections, drops, suppositories, inhalants, transmucosal absorbents, percutaneous absorbents, nose drops, ear drops, etc.

The form of the drug according to the invention, pharmaceutical additives to be used in the drug, the process for manufacturing the drug and the like are all within the skill of the art. The dosage of the drug according to the invention can be suitably selected in consideration of all of patients' sex, age, weight, severity of disease, purpose of administration such as prevention or therapies, other complications, etc. The dosage is generally in the range from 0.001 μg per kg of weight per day to 1000 μg per kg of weight per day, preferably from 0.01 μg per kg of weight per day to 100 μg per kg of weight per day.

BEST MODE OF CARRYING OUT THE INVENTION

The invention will be described in greater detail with reference to Reference Example, Example and Test Example to which, however, the invention is not limited.

$^1$H NMR was determined by AVANCE 400(indicated as 400 MHz) of Bruker. When a heavy solvent was used, the solvent peak was taken as the standard. The chemical shift was indicated as δ (ppm) and the binding constant was referred to as J(Hz). DC-Platten Kiesegel 60 F254 (Art 1,05715) manufactured by E. Merck was used for a reaction detection (hereinafter referred to as "TLC"). Used as a column for high performance liquid chromatography (HPLC) was COSMOSIL PACKED ODS COLUMN (Ø4.6×150 mm) manufactured by Nacalai Tesque, Inc., Shodex C18-5B manufactured by Showa Denko K.K. Used as a fluorescence spectrophotometer was FP 210 Spectrofluorometer manufactured by JASCO, Inc.

REFERENCE EXAMPLE 1

Preparation of Asparagine-linked Disialoundecaoligosaccharide-1

In 7.15 ml of a tris-hydrochloric acid-calcium chloride buffer (TRIZUMA BASE 0.05 mol/l, calcium chloride 0.01 mol/l, pH 7.5) were dissolved a crude SGP (sialyl glycopeptide) (238.3 mg, 80.6 µmol), and sodium azide (4.77 mg, 80.8 µmol). Then Actinase-E (53.8 mg) was added to the solution, and the mixture was allowed to react at 37° C. After 165 hours, the completion of reaction was confirmed by TLC and the reaction mixture was filtered. Then the filtrate was freeze-dried. Thereafter the residue was purified by gel filtration column chromatography (Sephadex G-25, Ø2.5 cm×100 cm) to give a desired asparagine-linked disialoundecaoligosaccharide 1 (yield 100.5 mg, 53%).

$^1$H-NMR (400 MHz, D$_2$O) δ 5.22(1H, s, Man4-H1), 5.16 (1H, d, J=9.6 Hz, GlcNAc-H$_1$), 5.04(1H, s, Man4'-H$_1$), 4.86 (1H, s, Man3-H$_1$), 4.70-4.68(3H, m, GlcNAc2-H$_1$ GlcNAc5, 5'-H$_1$), 4.53(2H, d, J=6.7 Hz, Gal6,6'-H$_1$), 4.34(1H, bd, Man3-H$_2$), 4.28(1H, bd, Man4'-H$_2$), 4.20(1H, bd, Man4-H$_2$), 3.03(2H, dd, J=4.2 Hz, 17.2 Hz, Asn-βCH), 2.95(2H, dd, J=6.9 Hz, 17.1 Hz, Asn-βCH), 2.76(2H, dd, J=4.6 Hz, 12.4 Hz, NeuAc7,7'-H$_{3eq}$), 2.14(18H, s×6, -Ac), 1.80(2H, dd, J=12.2 Hz, 12.1 Hz, NeuAc7,7'-H3ax)

EXAMPLE 1

Preparation of Asparagine-linked Disialoundecaoligosaccharide-decanoic Acid Amide 3

Decanoic acid (22 mg, 127.6 µmol) was dissolved in 1 ml of dimethylformamide. To the solution were added dicyclohexyl carbodiimide (23.9 mg, 115.8 µmol) and N-hydroxysuccinimide (13.4 mg, 116.4 µmol). The mixture was reacted at room temperature. After 6 hours, the reaction mixture was filtered, and the filtrate was concentrated. Then the residue (decanoic acid succinimide) was taken out. Then asparagine-linked disialoundecaoligosaccharide 1 (10.0 mg, 4.27 µmol) was dissolved in water (0.8 ml). Thereto added was sodium hydrogencarbonate (1.4 mg, 16.7 µmol). Then decanoic acid succinimide (3.2 mg, 11.8 µmol) dissolved in 1.2 ml of acetone was added thereto. The mixture was stirred at room temperature. After 180 minutes, it was confirmed by TLC that the raw material disappeared. Then the solution was freeze-dried. After it was freeze-dried, the residue was purified by gel filtration column chromatography (Sephadex G-25, 527 1.0 cm×20 cm), and freeze-dried. Thereafter it was purified by high performance liquid chromatography (ODS column, Ø4.6×150 mm, eluent: gradient (60 minutes) water 100%→acetonitrile 100%, flow rate 1.0 ml/min) to give the contemplated decanoic acid-asparagine-linked disialoundecaoligosaccharide 3 (yield 7.7 mg, 72%).

$^1$H-NMR (400 MHz, D$_2$O) δ 5.23(1H, s, Man4-H$_1$), 5.12 (1H, d, J=9.6 Hz, GlcNAc-H$_1$), 5.04(1H, s, Man4'-H$_1$), 4.87 (1H, s, Man3-H$_1$), 4.71-4.69(3H, m, GlcNAc2-H$_1$ GlcNAc5, 5'-H$_1$), 4.59(1H, dd, J=4.5 Hz, 8.0 Hz, Asn-αCH), 4.53(2H, d, J=7.9 Hz, Gal6,6'-H$_1$), 4.34(1H, bd, Man3-H$_2$), 4.29(1H, bd, Man4'-H$_2$), 4.21(1H, bd, Man4-H$_2$), 2.88(2H, dd, J=4.4 Hz, 15.5 Hz, Asn-βCH), 2.78-2.70(3H, m, NeuAc7,7'-H$_{3eq}$, Asn-βCH), 2.34(2H, t, J=7.4 Hz, COCH$_2$), 2.14(18H, s×6, —Ac), 1.80(2H, dd, J=12.2 Hz, 12.0 Hz, NeuAc7,7'-H$_{3ax}$), 1.71-1.60 (2H, m, CH$_2$), 1.42-1.30(12H, m, CH$_2$), 0.95(3H, t, J=6.5 Hz, CH$_3$)

EXAMPLE 2

Preparation of Asparagine-linked Disialoundecaoligosaccharide-myristic Acid Amide Myristic acid (22 mg, 96.3 µmol) was dissolved in 1 ml of dimethylformamide. To the solution were added dicyclohexyl carbodiimide (18.2 mg, 88.2 µmol) and N-hydroxybenzotriazole (11.9 mg, 96.7 µmol). The mixture was reacted at room temperature. After 6 hours, the reaction mixture was filtered, and the filtrate was concentrated. Then the residue (myristic acid benzotriazole) was taken out. Then asparagine-linked disialoundecaoligosaccharide 1 (6 mg, 2.57 µmol) was dissolved in water (0.8 ml). Thereto added was sodium hydrogencarbonate (0.86 mg, 10.3 µmol ). Then myristic acid benzotriazole (2.8 mg, 7.70 µmol) dissolved in 1.2 ml of acetone was added thereto. The mixture was stirred at room temperature. After 180 minutes, it was confirmed by TLC that the raw material disappeared. Then the solution was freeze-dried. After it was freeze-dried, the residue was purified by gel filtration column chromatography (Sephadex G-25, Ø1.0 cm×20 cm), and freeze-dried. Thereafter it was purified by high performance liquid chromatography (ODS column, Ø4.6×150 mm, eluent: gradient (60 minutes) water 100%→acetonitrile 100%, flow rate 1.0 ml/min) to give the contemplated myristic acid-asparagine-linked disialoundecaoligosaccharide 4 (yield 5.3 mg, 81%).

$^1$H-NMR (400 MHz, D$_2$O) δ 5.23(1H, s, Man4-H$_1$), 5.12 (1H, d, J=9.6 Hz, GlcNAc-H$_1$), 5.04(1H, s, Man4'-H$_1$), 4.87 (1H, s, Man3-H$_1$), 4.70-4.69(3H, m, GlcNAc2-H$_1$ GlcNAc5, 5'-H$_1$), 4.59(1H, dd, J=4.6 Hz, 8.1 Hz, Asn-αCH), 4.54(2H, d, J=7.8 Hz, Gal6,6'-H$_1$), 4.34(1H, bd, Man3-H$_2$), 4.29(1H, bd, Man4'-H$_2$), 4.20(1H, bd, Man4-H$_2$), 2.88(2H, dd, J=4.6 Hz, 15.6 Hz, Asn-βCH), 2.83-2.70(3H, m, NeuAc7,7'-H$_{3eq}$, Asn-βCH), 2.34(2H, t, J=7.4 Hz, COCH$_2$), 2.14(18H, s×6, —Ac), 1.80(2H, dd, J=12.1 Hz, 12.1 Hz, NeuAc7,7'-H$_{3ax}$), 1.71-1.60 (2H, m, CH$_2$), 1.42-1.30(20H, m, CH$_2$), 0.95(3H, t, J=6.5 Hz, CH$_3$)

EXAMPLE 3

Preparation of Asparagine-linked Disialoundecaoligosaccharide-stearic Acid Amide 5

Stearic acid (22.0 mg, 77.3 µmol) was dissolved in 1 ml of dimethylformamide. To the solution were added dicyclohexyl carbodiimide (14.4 mg, 69.8 µmol) and N-hydroxybenzotriazole (9.5 mg, 77.2 µmol). The mixture was reacted at room temperature. After 6 hours, the reaction mixture was filtered, and the filtrate was concentrated. Then the residue (stearic acid benzotriazole) was taken out. Then asparagine-linked disialoundecaoligosaccharide 1 (8.0 mg, 3.36 µmol) was dissolved in water (1.2 ml). Thereto added was sodium hydrogencarbonate (3.2 mg, 38.1 µmol). Then stearic acid benzotriazole (8.8 mg, 20.2 µmol) dissolved in 1.8 ml of acetone was added thereto. The mixture was stirred at 37° C. After 195 minutes, it was confirmed by TLC that the reaction has completed. Then the solution was freeze-dried. After it was freeze-dried, the residue was purified by gel filtration column chromatography (Sephadex G-25, Ø1.0 cm×20 cm), and freeze-dried. Thereafter it was purified by high performance liquid chromatography (ODS column, Ø4.6×150 mm, eluent: gradient (60 minutes) water 100%→acetonitrile 100%, flow rate 1.0 ml/min) to give the contemplated stearic acid-asparagine-linked disialoundecaoligosaccharide 5 (yield 6.2 mg, 69%).

$^1$H-NMR (400 MHz, D$_2$O) δ 5.23(1H, s, Man4-H$_1$), 5.12 (1H, d, J=9.5 Hz, GlcNAc-H$_1$), 5.04(1H, s, Man4'-H$_1$), 4.86 (1H, s, Man3-H$_1$), 4.71-4.69(3H, m, GlcNAc2-H$_1$ GlcNAc5, 5'-H$_1$), 4.59(1H, dd, J=4.6 Hz, 8.2 Hz, Asn-αCH), 4.54(2H, d, J=7.8 Hz, Gal6,6'-H$_1$), 4.34(1H, bd, Man3-H$_2$), 4.29(1H, bd, Man4'-H$_2$), 4.20(1H, bd, Man4-H$_2$), 2.88(2H, dd, J=4.7 Hz, 15.5 Hz, Asn-βCH), 2.78-2.70(3H, m, NeuAc7,7'-H$_{3eq}$AsnβCH), 2.34(2H, t, J=7.3 Hz, COCH$_2$), 2.16(18H, s×6, —Ac), 1.80(2H, dd, J=12.1 Hz, 12.1 Hz, NeuAc7,7'-H$_{3ax}$), 1.71-1.60(2H, m, CH$_2$), 1.42-1.30(28H, m, CH$_2$), 0.96 (3H, t, J=6.7 Hz, CH$_3$)

EXAMPLE 4

Preparation of Asparagine-linked Disialoundecaoligosaccharide-behenic Acid Amide 6

Behenic acid (20.0 mg, 58.7 μmol) was dissolved in 3 ml of dimethylformamide. To the solution were added dicyclohexyl carbodiimide (10.3 mg, 50.0 μmol) and N-hydroxybenzotriazole (6.8 mg, 50.3 μmol). The mixture was reacted at room temperature. After 19 hours, the reaction mixture was filtered, and the filtrate was concentrated. Then the residue (behenic acid benzotriazole) was taken out. Then asparagine-linked disialoundecaoligosaccharide 1 (5 mg, 2.1 μmol) was dissolved in water (1.2 ml). Thereto added was sodium hydrogencarbonate (2.0 mg, 21.0 μmol). Then behenic acid benzotriazole (8.8 mg, 18.9 μmol) dissolved in 1.8 ml of acetone was added thereto. The mixture was stirred at 37° C. After 20 hours, it was confirmed by TLC that the reaction has completed. Then the solution was freeze-dried. After it was freeze-dried, the residue was purified by gel filtration column chromatography (Sephadex G-25, Ø1.0 cm×20 cm), and freeze-dried. Thereafter it was purified by high performance liquid chromatography (ODS column, Ø4.6×150 mm, eluent: gradient (60 minutes) water 100%→acetonitrile 100%, flow rate 1.0 ml/min) to give the contemplated behenic acid-asparagine-linked disialoundecaoligosaccharide 6 (yield 3.24 mg, 57%).

$^1$H-NMR(400 MHz, D$_2$O) δ 5.23(1H, s, Man4-H$_1$), 5.12 (1H, d, J=9.2 Hz, GlcNAc-H$_1$), 5.04(1H, s, Man4'-H$_1$), 4.86 (1H, s, Man3-H$_1$), 4.70-4.69(3H, m, GlcNAc2-H$_1$ GlcNAc5, 5'-H$_1$), 4.59(1H, dd, J=4.5 Hz, 8.0 Hz, Asn-αCH), 4.54(2H, d, J=7.4 Hz, Gal6,6'-H$_1$), 4.34(1H, bd, Man3-H$_2$), 4.29(1H, bd, Man4'-H$_2$), 4.21(1H, bd, Man4-H$_2$), 2.88(2H, dd, J=4.4 Hz, 16.4 Hz, Asn-βCH), 2.78-2.70(3H, m, NeuAc7,7'-H$_{3eq}$, Asn-βCH), 2.35(2H, t, J=7.3 Hz, COCH$_2$), 2.13(18H, s×6, —Ac), 1.80(2H, dd, J=12.1 Hz, 12.0 Hz, NeuAc7,7'-H3ax), 1.71-1.60(2H, m, CH$_2$), 1.42-1.30(36H, m, CH$_2$), 0.95(3H, t, J=6.6 Hz, CH$_3$)

Figure 2:
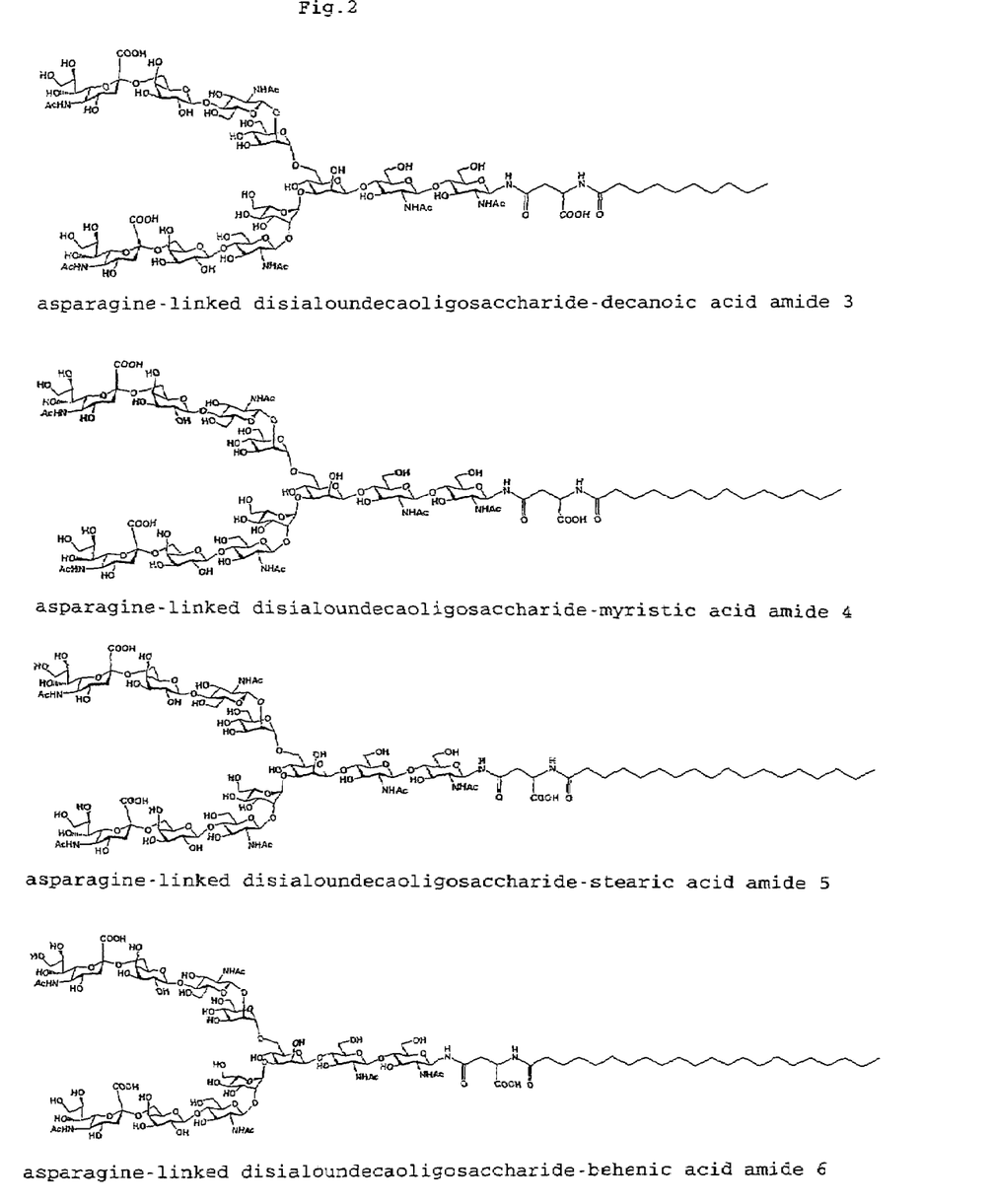
FIG. 2 shows the chemical formula of each of asparagine-linked disialoundecaoligosaccharide-fatty acid amides prepared in Examples 1 to 4.

FIG. 2 shows chemical formula of each asparagine-linked disialoundecaoligosaccharide-fatty acid amide of Examples 1 to 4.

TEST EXAMPLE 1

Measurement of Sialidase Inhibition Activity of Inhibitor against Influenza Virus Infection (1) Sialylation of Fluorescent-labelled N-acetyl Lactosamine Derivative It was investigated whether asparagine-linked disialoundecaoligosaccharide-fatty acid amide is really made into a micell in an aqueous solution. For this purpose, the sialidase inhibition activity was measured with respect to fluorescent-labelled sialyl oligosaccharide to determine the IC$_{50}$. If the asparagine-linked disialoundecaoligosaccharide 1, and four synthesized glicolipid derivatives, respectively were made to coexist with fluorescent-labelled sialyl saccharide 7 to determine the sialidase inhibition activity and if the inhibition activity is increased depending on the length of carbon chain, it is presumably the effect of micell creation. First, fluorescent-labelled sialyl oligosaccharide was produced. Dansyl group was used for fluorescent-labelling. There was synthesized 6-[(N-Dansyl)amino]-hexyl-O-β-D-galactopylanosyl-(1→4)-2-acetoamido-2-deoxy-β-D-glucopyranoside (hereinafter referred to as "Dansyl-LacNac") in which N-acetyllactosamine derivative was labelled with Dansyl. Sialic acid was transferred to galactose using α(2,6) sialyltransferase to give Dansyl-labelled sialyl oligosaccharide (hereinafter referred to as "NeuAc-LacNAc-Dansyl").

Figure 3:
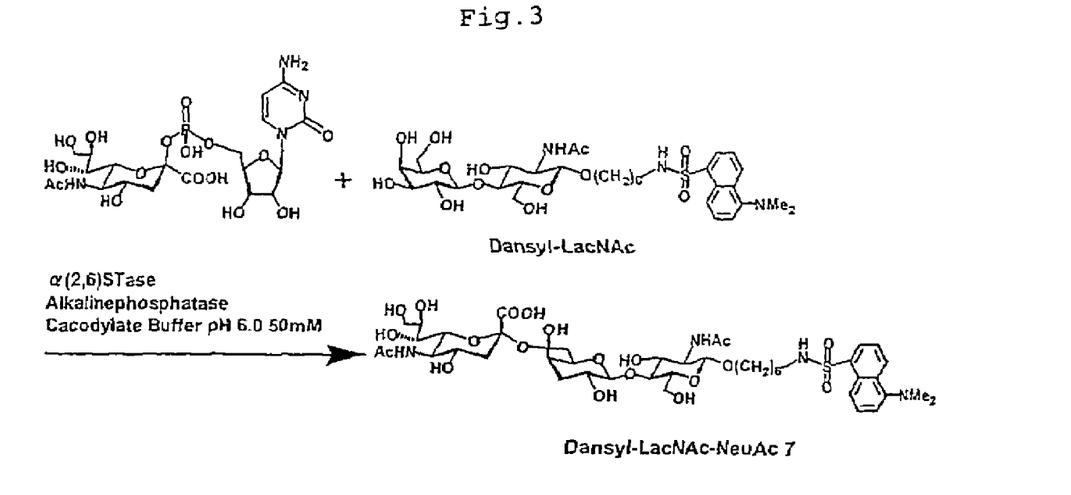
FIG. 3 shows a reaction scheme for producing sialylated Dansyl-LacNAc.

Dissolved in cacodylic acid buffer (pH 6.0, 50 mM) were Dansyl-LacNAc, CMP-sialic acid, α (2,6) sialyltransferase, alkaline phosphatase and bovine serum alubmin. Then the solution was reacted at 37° C. for 65 hours and purified by high performance liquid chromatography, giving NeuAc-LacNAc-Dansyl 7 in a yield of 69%. $^1$H NMR of the compound 7 was measured. It was confirmed that 3-position equatorial peak and axial proton peak (peaks specific to sialic acid) existed in 2.74 ppm and 1.80 ppm. When it was compared with $^1$H NMR of raw material Dansyl-LacNAc, the 1-position proton peak of galactose of compound 7 was shifted, as compared with the peak of the raw material, to the higher magnetic field, so that it was found that sialic acid was bonded to 6-position of galactose. In this way, the compound 7 was identified. The foregoing reaction is shown in FIG. 3.

Figure 4:
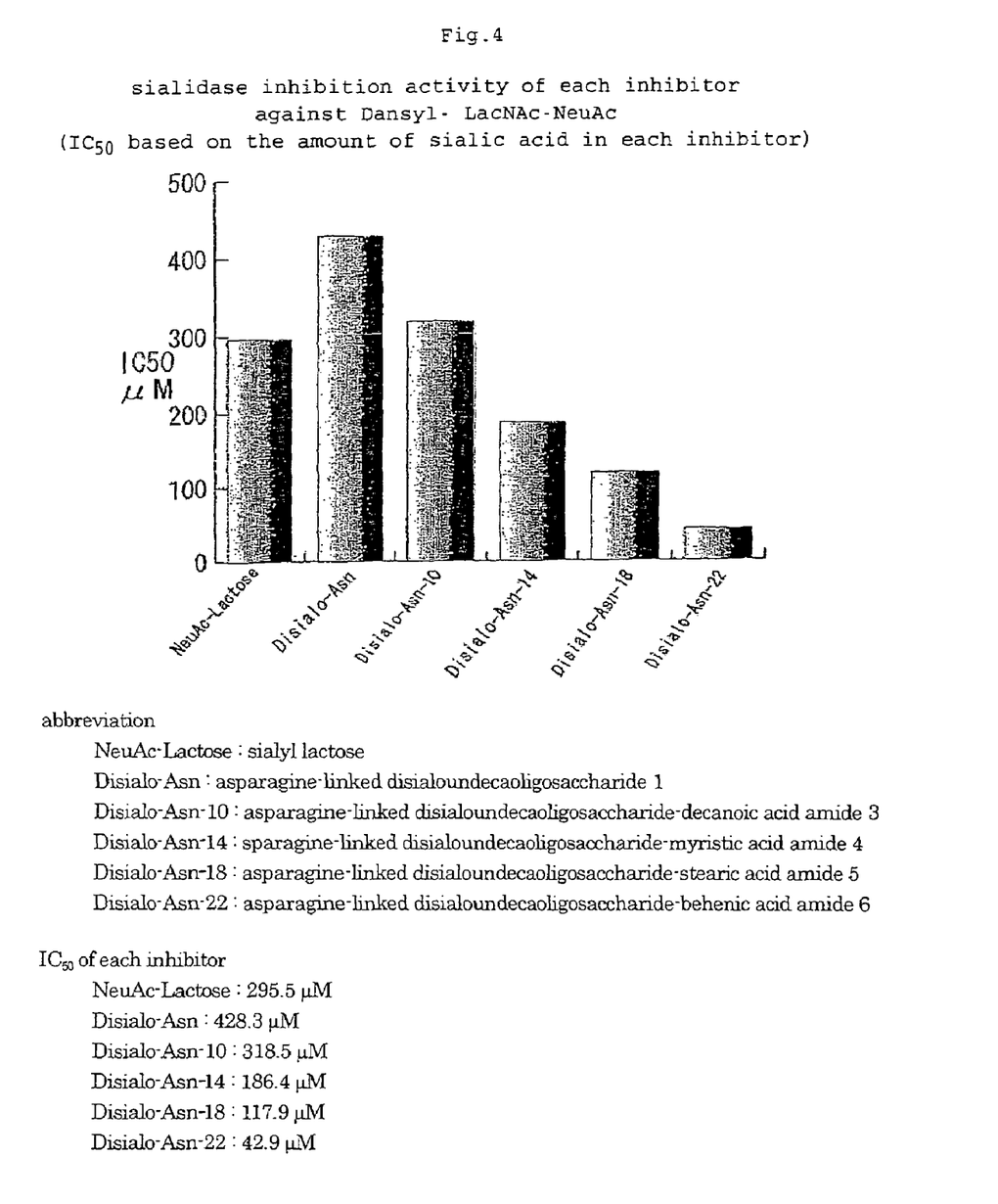
FIG. 4 shows the sialidase inhibition activity, based on the amount of sialic acid in each inhibitor.

(2) Measurement of Sialidase Inhibition Activity of Asparagine-linked Disialoundecaoligosaccharide-fatty Acide Amide In an experiment wherein NeuAc-LacNAc-Dansyl is hydrolyzed with sialidase, the synthesized glycolipid derivatives 3, 4, 5 and 6, sialyl lactose, and asparagine-linked disialoundecaoligosaccharide 1 were added as the inhibitor, and each of the IC$_{50}$ values was determined. The reaction conditions are as follows. Added to 100 μM of NeuAc-LacNAc-Dansyl was each of inhibitors in an amount of each of 10 μM, 100 μM and 300 μM (the solvent was a solution of HEPES buffer having bovine serum albumin dissolved therein). Then sialidase was added and the mixture was incubated at 37° C. for 30 minutes. The decomposition ratio of fluorescent-labelled NeuAc-LacNAc-Dansyl was determined by high performance liquid chromatography and IC$_{50}$ was calculated from the resulting values. The results were summarized with substrate by substrate. The concentration of the inhibitor required for inhibiting the enzyme reaction by 50% (IC$_{50}$) is plotted as ordinates. The graph of FIG. 4 indicates the results of determining the IC$_{50}$ with the amount of sialic acid in the reaction system. Since asparagine-linked disialoundecaoligosaccharide contains two sialic acids in a molecule, the measured values in determining IC$_{50}$ are twice the amount of sialic acid. It is as shown in FIG. 4.

Figure 5:
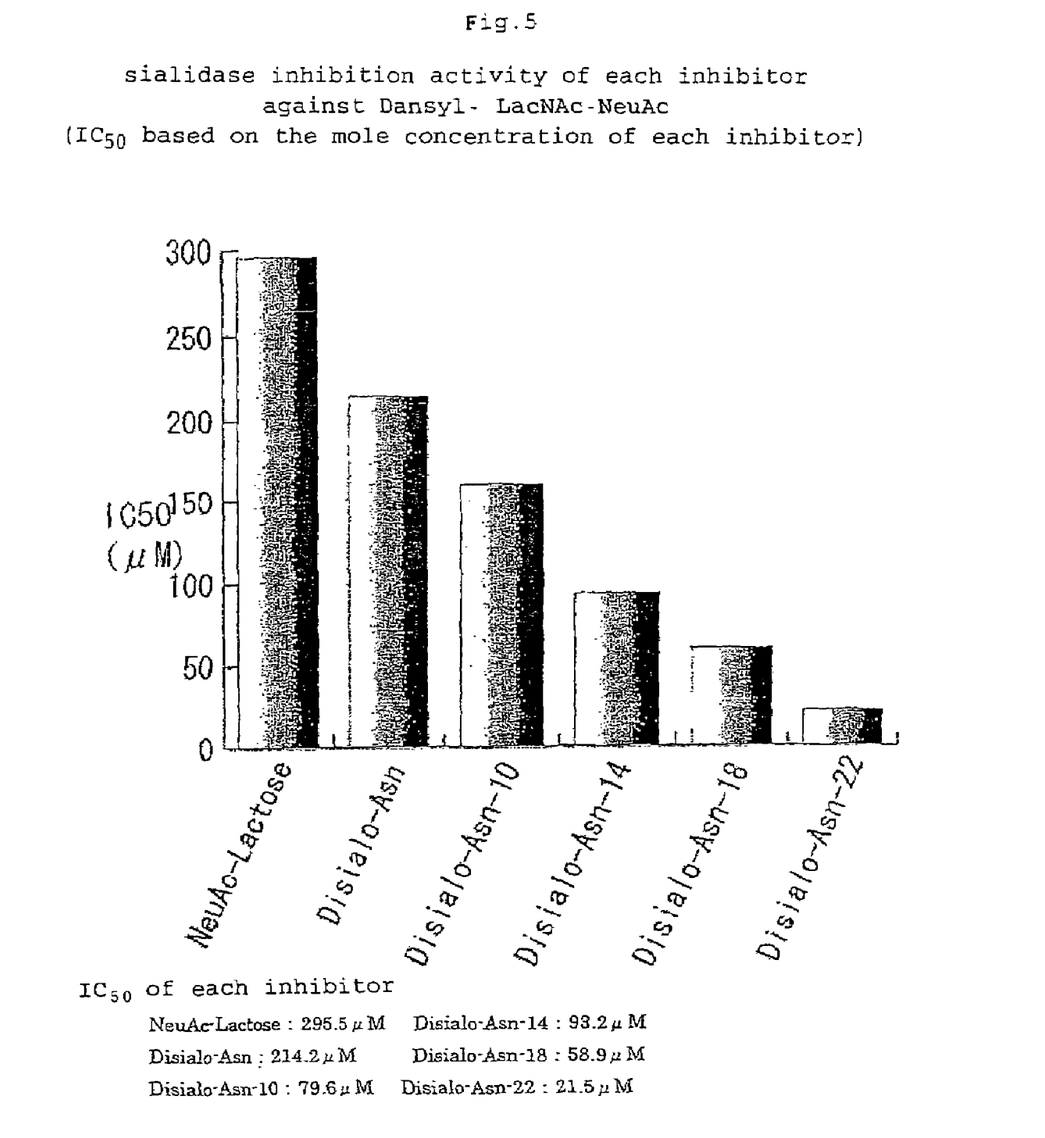
FIG. 5 shows the sialidase inhibition activity, based on the mole concentration of each inhibitor.

The measured IC$_{50}$ with respect to mole concentrations of these inhibitors were determined. The IC$_{50}$ of inhibitors other than sialyl lactose is half the value of FIG. 4 (FIG. 5). It was understood from the graph of FIG. 4 that only when decanoic acid having the shortest carbon chain is bonded to asparagine-linked disialoundecaoligosaccharide 1 as a hydrophobic group, the value of IC$_{50}$ is ¾ the value of asparagine-linked disialoundecaoligosaccharide 1 to which no hydrophobic group is bonded. This is presumably for the following reason. Carboxylic acid as a hydrophobic group is bonded to asparagine-linked disialoundecaoligosaccharide as a hydrophilic group, whereby the compound is made into a micell and numerous asparagine-linked disialoundecaoligosaccharide are contained in one molecule. This means that the frequency of being caught by sialidase is increased, and the capability of inhibiting the removal of sialic acid by NeuAc-LacNAc-Dansyl is presumably enhanced. It was also found that the longer the carbon chain of hydrophobic group becomes (decanoic acid→myristic acid→stearic acid→behenic acid), the systematically lower the value of $IC_{50}$ becomes. The reason may be that the longer the carbon chain of hydrophobic group becomes, the larger the surface area of the micell bodies become and the more the number of asparagine-linked disialoundecaoligosaccharide in the surface of the molecule becomes, and the higher the capability of inhibiting the hydrolysis of sialic acid by NeuAc-LacNAc-Dansyl presumably is. It was also found from FIG. 5 that only when the number of sialyl lactone is increased in the molecule only by one, the sialidase inhibition activity is enhanced, and the longer the carbon chain is, the higher the effect is.

(3) Measurement of Influenza Virus Inhibiting Activity of Asparagine-linked Disialoundecaoligosaccharide-fatty Acid Amide With addition of each of asparagine-linked disialoundecaoligosaccharide-fatty acid amides of Examples 1 to 4 (derivatives 3, 4, 5 and 6 in FIG. 2) as an inhibitor, the influenza virus (hemagglutinin) inhibiting activity was determined.

The reaction conditions are as follows.

The influenza virus used was A/New Caledonia/20/99 (H1N1).

The sample was inoculated with fertilized fowl ovum and the chorioallantois fluid was collected. After ultracentifuge purification and formalin inactivation, the obtained sample was used as as a purified virus antigen. Then after treatment with ether, HA (hemagglutinin) fractions were collected to give HA split fractions.

1) Two mg of each of derivatives 3, 4, 5 and 6 of FIG. 2 was dissolved in 1 ml of PBS.

2) The sample was used as it was or as diluted 2-fold, 4-fold, or 8-fold with PBS.

3) 10 µl of each sample and 40 µl of virus diluted solution were placed and mixed in a 96-well U plate (Sanko Junyaku Co., Ltd.).

4) The mixture was allowed to stand at 4° C. for 60 minutes.

5) 50 µl of PBS was added to the mixture to give 50 µl of 2-fold dilution solution.

6) The solution was adjusted to 0.5% of fowl hematid (Nippon Biotest Laboratories Inc.).

7) 50 µl of blood cell suspension was applied to each well to give a mixture. The mixture was allowed to stand at 4° C. for 60 minutes.

8) The measurement of influenza virus (hemagglutinin) inhibiting activity shows that the inhibiting activity was exhibited when each derivative was used in the following amount: 190.0 µmol of derivative 3; 95.0 µmol of derivative 4; 47.5 µmol of derivative 5; and 37.5 µmol of derivative 6.

INDUSTRIAL APPLICABILITY

The asparagine-linked disialoundecaoligosaccharide-fatty acid amide and asparagine-linked disialoundecaoligosaccharide according to the invention have a high virus infection inhibiting activity and/or growth inhibiting activity and, for example, exhibit an excellent effect as a drug for preventing and/or curing virus diseases such as influenza virus infectious diseases.

The invention claimed is:

1. An asparagine-linked disialoundecaoligosaccharide-fatty acid amide which does not have an amino acid other than the asparagine, wherein the disialoundecaoligosaccharide has the formula:

and wherein the fatty acid is one having 8 to 24 carbon atoms.

2. An asparagine-linked disialoundecaoligosaccharide-fatty acid amide according to claim 1 wherein the fatty acid is one having 10 to 22 carbon atoms.

3. An asparagine-linked disialoundecaoligosaccharide-fatty acid amide according to claim 2 wherein the fatty acid is at least one selected from the group consisting of capric acid, lauric acid, myristic acid, palmitic acid, stearic acid, arachic acid, behenic acid and oleic acid.

4. A composition comprising asparagine-linked disialoundecaoligosaccharide-fatty acid amide of claim 1 and a pharmaceutical additive.

5. A composition according to claim 4 wherein the pharmaceutical additive is at least one selected from the group consisting of lactose, glycerin, glucose, sucrose and mannitol.

6. A drug containing the asparagine-linked disialoundecaoligosaccharide-fatty acid amide of claim 1.

7. A drug comprising at least one selected from asparagine-linked disialoundecaoligosaccharide-fatty acid amide of claim 1 and asparagine-linked disialoundecaoligosaccharide having formula 3:

and a pharmaceutical additive.

8. A composition comprising asparagine-linked disialoundecaoligosaccharide-fatty acid amide of claim 2, and a pharmaceutical additive.

9. A composition comprising asparagine-linked disialoundecaoligosaccharide-fatty acid amide of claim 3, and a pharmaceutical additive.

10. A composition according to claim 8 wherein the pharmaceutical additive is at least one selected from the group consisting of lactose, glycerin, glucose, sucrose and mannitol.

11. A composition according to claim 9 wherein the pharmaceutical additive is at least one selected from the group consisting of lactose, glycerin, glucose, sucrose and mannitol.

12. A method of treating influenza comprising administering a therapeutically effectively amount of an asparagine-linked disialoundecaoligosaccharide-fatty acid amide of claim 1 to a subject in need of such treatment.

13. A method of treating influenza comprising administering a therapeutically effective amount of an asparagine-linked disialoundecaoligosaccharide-fatty acid amide of claim 2 to a subject in need of such treatment.

14. A method of treating influenza comprising administering a therapeutically effective amount of an asparagine-linked disialoundecaoligosaccharide-fatty acid amide of claim 3 to a subject in need of such treatment.

15. A method of treating influenza comprising administering a therapeutically effective amount of a composition of claim 4 to a subject in need of such treatment.

16. A method of treating influenza comprising administering a therapeutically effective amount of a composition of claim 5 to a subject in need of such treatment.

17. A method of treating influenza comprising administering a therapeutically effective amount of a composition of claim 8 to a subject in need of such treatment.

18. A method of treating influenza comprising administering a therapeutically effective amount of a composition of claim 9 to a subject in need of such treatment.

19. A method of treating influenza comprising administering a therapeutically effective amount of a composition of claim 10 to a subject in need of such treatment.

20. A method of treating influenza comprising administering a therapeutically effective amount of a composition of claim 11 to a subject in need of such treatment.

21. A method of treating influenza comprising administering a therapeutically effective amount of a drug of claim 6 to a subject in need of such treatment.

22. A method of treating influenza comprising administering a therapeutically effective amount of a drug of claim 7 to a subject in need of such treatment.

* * * * *

UNITED STATES PATENT AND TRADEMARK OFFICE
CERTIFICATE OF CORRECTION

PATENT NO. : 7,687,478 B2  Page 1 of 1
APPLICATION NO. : 10/562059
DATED : March 30, 2010
INVENTOR(S) : Kajihara et al.

It is certified that error appears in the above-identified patent and that said Letters Patent is hereby corrected as shown below:

In the Claims:

Column 12, Claim 1, Line 35: Please correct formula by adding -- HO- -- where indicated:

Signed and Sealed this

Sixth Day of July, 2010

David J. Kappos
*Director of the United States Patent and Trademark Office*